United States Patent [19]
Viñas Almenar et al.

[11] Patent Number: 5,843,434
[45] Date of Patent: Dec. 1, 1998

[54] **STRAIN OF THE YEAST *CANDIDA SAKE* (SAITO AND OTA) VAN UDEN AND BUCKLEY AND ITS USE AS A BIOLOGICAL CONTROL AGENT FOR POST-HARVEST FUNGA L DISEASES IN FRUITS**

[75] Inventors: Inmaculada Viñas Almenar, Lleida; Josep Usall I Rodie, Alguaire; Neus Teixido I Espasa, Seros; Vicente Sanchis Almenar, Lieida, all of Spain

[73] Assignee: Sipcam Inagra, S.A., Valencia, Spain

[21] Appl. No.: 757,583

[22] Filed: Nov. 27, 1996

Related U.S. Application Data

[63] Continuation of PCT/ES96/00064, Mar. 25, 1996.
[51] Int. Cl.⁶ .......................... A01N 63/00; A01N 63/04; C12N 1/14
[52] U.S. Cl. ..................................... 424/93.51; 435/255.4
[58] Field of Search ................................ 426/52, 62, 656; 435/255.1, 255.4; 424/93.51

[56] References Cited

U.S. PATENT DOCUMENTS 5,633,025  5/1997  Ghaoth et al. ............................. 426/62
7,745,796  8/1991  Wilson .

OTHER PUBLICATIONS

Jijakli et al., "Biological Control of *Botyrtis cincerea* and Penicillium sp. on Post–Harvest Apples by Two Anatagonistic Yeast", Med. Fac. Landbouww, Univ. Gent., vol. 58, pp. 1349–1358, 1993.

Wilson et al., "A selection Strategy for Microbial Antagonists to Control Postharvest Diseases of Fruits and Vegtables", Scientia Horticulturae, vol. 53, pp. 188–189, Feb. 1993.

*Primary Examiner*—Marian C. Knode
*Assistant Examiner*—Brenda G. Brumback
*Attorney, Agent, or Firm*—Michael J. Striker

[57] ABSTRACT

A new strain of the yeast *Candida sake* (Saito and Ota) van Uden and Buckley and its properties are described. This new strain was deposited with number CECT-10817. Rotting of fruit caused by at least one pathogenic fungi, particularly *Botrytis cinera, Penicillium expansum* or *Rhizopus nigricans*, after or before harvesting, can be prevented by treating the fruit with an aqueous dispersion of this new strain of *Candida sake*.

21 Claims, 7 Drawing Sheets

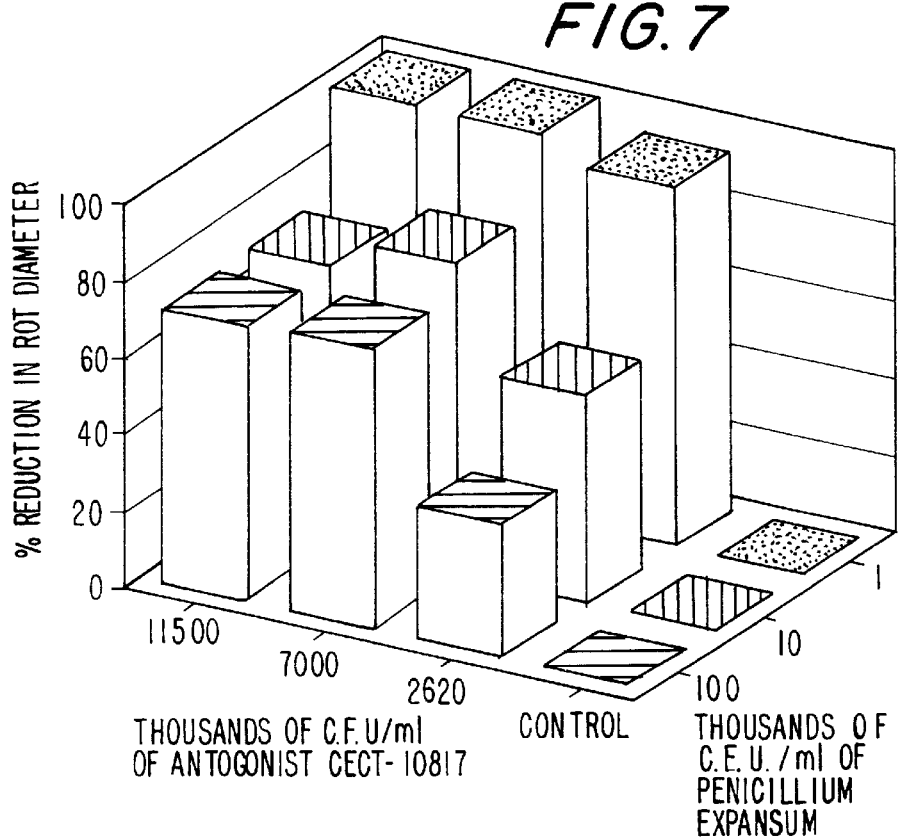
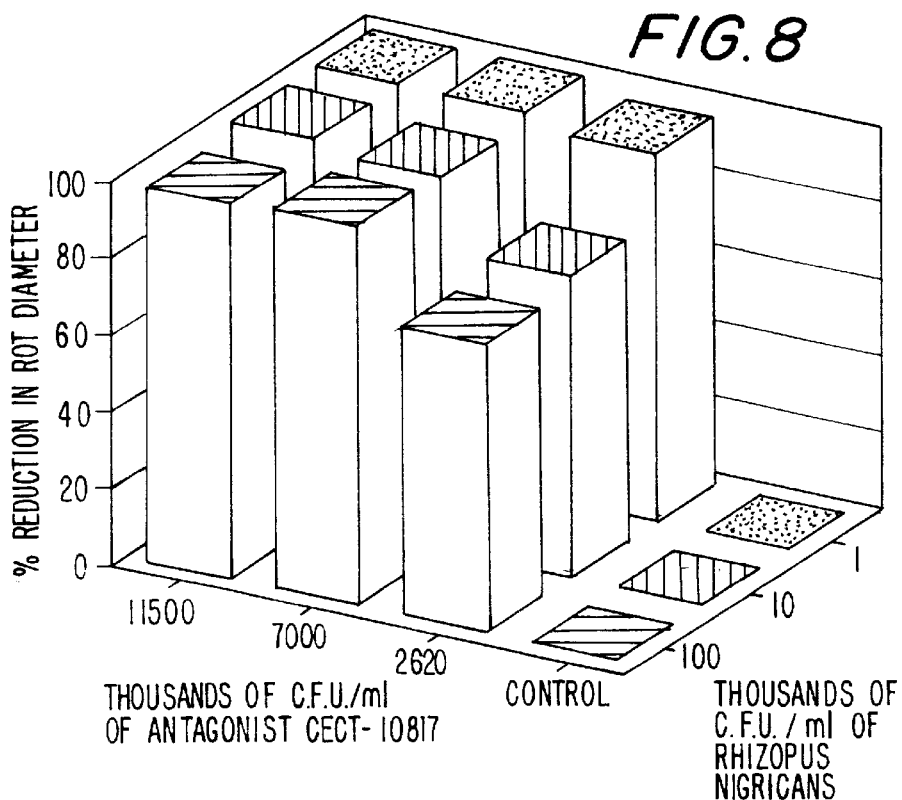

STRAIN OF THE YEAST *CANDIDA SAKE* (SAITO AND OTA) VAN UDEN AND BUCKLEY AND ITS USE AS A BIOLOGICAL CONTROL AGENT FOR POST-HARVEST FUNGA L DISEASES IN FRUITS

CROSS-REFERENCE

This is a continuation of the International Patent application, PCT/ES 96/00064, filed Mar. 25, 1996, now abandoned.

BACKGROUND OF THE INVENTION

1. Field of the Invention

The present invention relates to a new strain of the yeast *Candida sake* and its use as an antagonist in the biological control of fungal diseases of harvested fruit, with the object of preventing rotting of the fruit under storage conditions.

2. Prior Art

Post-harvest diseases of fruits cause annual losses in agriculture estimated at a quantity of the order of 15% to 20% of total harvests worldwide.

The most widely used system at present for combatting the fungi which cause rotting of the fruits after harvesting is chemical control by means of treatment of the harvests with fungicidal products. The use of fungicides is quite widespread throughout the world, being estimated to represent up to 26% of the pesticides in the European and Asiatic markets, and up to 6% in the North American market.

The large-scale utilization of said fungicidal products has led to a number of problems, such as the emergence of resistant pathogenic strains—which leads to a steady rise in the cost of treatments and to increased losses due to rotting—and an increase of fungicide residues on the fruits, which gives rise to health problems and hinders exports to countries which have restrictive health regulations in this sphere.

Faced with this problem, research work began a relatively few years ago in order to find new alternative methods for the control of fruit diseases in the post-harvest phase, with one of the most notable development paths lying in biological control of the fungi which cause the rotting. The biological control is based on the inhibiting action of some microorganisms on the growth and action of the pathogenic fungi. Thus, Janisiewicz, W. J., Phytopathology 77:481–485 (1987), reported a biological control treatment for blue mold of apples; Janisiewicz, W. J. and Roitman, J., Phytopathology, 77: 1776 (1987), reported the use of *Pseudomonas cepacia* as a post-harvest biocontrol agent to combat rotting of apples; Janisiewicz, W. J. and Roitman, J., Phytopathology, 78: 1697–1700 (1988), reported the use of *Pseudomonas cepacia* as a post-harvest biocontrol agent to combat grey and blue mold of apples and pears.

Amongst the antagonists of the fungi which cause rotting of fruit, the yeasts are of particular interest, in that they can colonize the surface of the fruit for long periods of time, producing extracellular polysaccharides which enhance their survival and limit the places of colonization and the germination of pathogenic fungi, owing to the fact that they use the available nutrients more rapidly. Thus, McLaughlin, R. J. et al., Phytopathology 80: 456–461 (1990), reported the effects of concentration of the *Candida sp.* yeasts in the biological control of post-harvest diseases of apples. Patent application PCT WO-91/1641 describes the use, as agents for the biological control of post-harvest diseases of vegetable products, of several yeasts, amongst them strains or isolates belonging to the species *Candida guilliermondii*. The isolates show activity against, amongst others, the following species of pathogenic fungi: *Penicillium italicum, Penicillium digitatum, Botrytis cinerea, Rhizopus stolonifer, Geotrichum candidum, Penicillium expansum* and *Alternaris alternata*. North American patent U.S. Pat. No. 5,041,384, which comes from the same priority as the aforesaid PCT patent application, centers on the activity of three specific strains of *Candida guilliermondii*.

Patent application PCT WO-92/18009 also describes the use of yeasts as biological control agents for post-harvest diseases in fruits, specifically citing isolates of the species *Rhodotorula glutinis, Rhodotorula mucilaginosa, Candida parapsilopis* and *Candida guilliermondii*. Finally, Wilson, C. L., in North American patent application U.S Pat. No. 7,745,796, published as NTIS (National Technical Information Service) document number PB92-102334, describes the use as biological control agents against post-harvest diseases of fruits such as apples, peaches and oranges, of three specific strains of *Candida sake*, isolated from the skin of tomatoes, deposited, in compliance with the Treaty of Budapest, at The Northern Regional Research Center U.S. Department of Agriculture, Peoria Ill. 61604, with deposit numbers NRRL Y-18844, NRRL Y-18845 and NRRL Y-18846.

However, the great differences of antifungic activity which can be shown between different isolates or strains of the same species and the lack of information about their effectiveness under the various storage conditions of harvested fruits, raises the need to continue research in order to find increasingly effective and longer-acting biological control agents which are capable of exercising their preventive action under extreme storage conditions.

SUMMARY OF THE INVENTION

The object of the present invention is to provide a new strain of the yeast *Candida sake* capable of acting as a highly effective antagonist in biological control of the pathogenic fungi responsible for the rotting of post-harvest fruit, and which retain their effectiveness under conditions of low temperature and low-oxygen atmosphere.

A further object of the present invention consists in the utilization of this new strain of *Candida sake* to prevent the rotting of harvested fruit, during storage of the fruit.

Yet another object of the invention consists in providing a method for better preservation of the harvested fruit under various storage conditions.

According to the invention, rotting of fruit caused by at least one pathogenic fungi, especially *Botrytis cinera, Penicillium expansum* or *Rhizopus nigricans*, after or before harvesting, is prevented by treating the fruit with a preparation containing a culture of the new strain of *Candida sake* designated CECT-10817.

In a preferred embodiment the preparation is an aqueous dispersion of the new strain of *Candida sake* and the treating is performed by means of spraying the fruit with the aqueous dispersion, wetting the fruit with the aqueous dispersion, immersing the fruit in the aqueous dispersion and/or inoculating the fruit with the aqueous dispersion In one embodiment for preparation of the aqueous dispersion the new strain can be cultured at pH 7 in NYDB culture medium at temperatures between 1° C. and 34° C. for 20 to 50 hours.

Although the method is effective for fruit stored at ambient conditions of temperature and oxygen, it is particularly effective for fruit stored at temperatures less than 5° C.

The method is effective against rotting of strawberries, pip fruit, citrus fruit or stone fruit caused by pathogenic fungi.

In a particularly preferred embodiment the rotting of fruit, particularly pip fruit, caused by *Rhizopus nigricans*, after or before harvesting the fruit, can be prevented by treating the fruit with an aqueous dispersion containing from about $10^5$ to $10^7$ C.F.U./ml of the new strain of *Candida sake*, designated CECT-10817.

BRIEF DESCRIPTION OF THE DRAWING

For a better understanding of same, this description is accompanied by seven sheets of drawings for which, without limiting effects, a brief outline is provided.

FIG. 7 is a three-dimensional bar-diagram view of the percentages of reduction of rotting, in "Golden Delicious" apples inoculated with *Penicillium expansum*, caused by inoculation of the antagonist CECT-10817. Data obtained following seven days of incubation at 20° C.

FIG. 8 is a three-dimensional bar-diagram view of the percentages of reduction of rotting, in "Golden Delicious" apples inoculated with *Rhizopus nigricans* caused by inoculation of the antagonist CECT-10817. Data obtained following six days of incubation at 20° C.

DESCRIPTION OF THE PREFERRED EMBODIMENTS

Figure 1:
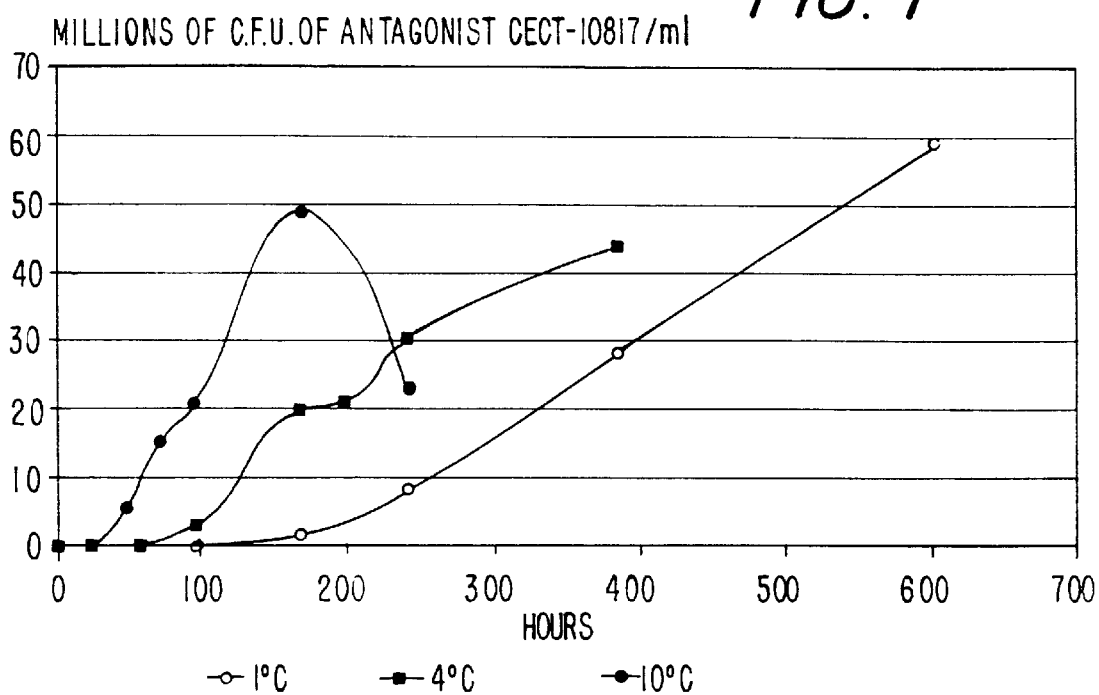
FIG. 1 is a graphic representation of the growth curve of the CECT-10817 strain, in NYDB medium, under low temperature conditions.

The authors of the present invention have managed to isolate a new strain of the species *Candida sake* (Saito and Ota) van Uden and Buckley which shows very high effectiveness as an antagonist of the species of fungi which cause diseases in post-harvest fruits, over a wide range of temperatures and oxygen atmospheres, which permits their industrial utilization for the biological control of the fungic species and the prevention of rotting of the fruit under storage conditions.

The new strain of *Candida sake* was isolated on the surface of apples, by means of repeated washings with sterile water, and a culture of same was deposited, in accordance with the provisions of the Treaty of Budapest on the recognition of deposition of microorganisms for the purpose of patent procedures, under the international depositing authority of Colección Española de Cultivos Tipo (Spanish Collection of Standard Cultures), situated in the Faculty of Biological Sciences, University of Valencia, 46100 Burjasot (Valencia), Spain, which assigned it deposit number CECT-10817.

The isolate of CECT-10817 was identified as *Candida sake* by the "Centraalbureau voor Schimmelcultures" of Holland and, following isolation thereof, was cultivated in the NYDA medium, consisting in yeast extract, dextrose and agar, and in the NYDB medium, consisting in broth of yeast extract and dextrose. The isolate of CECT-10817 forms colonies of creamy white color, round, well-defined, with smooth edge and with a slight central elevation, with pseudohyphae in the cultures.

The CECT-10817 strain presents the biochemical characteristics detailed in Tables I and II.

TABLE I

Oxidation tests

| | | | | | |
|---|---|---|---|---|---|
| Gentibiose | +(F) | D-Gluconic acid | – | N-Acetyl-D-Glucosamine | – |
| Melibiose | +(F) | Dextrin | – | Alpha-D-Glucose | – |
| L-Proline | + | Inulin | – | D-Galactose | – |
| Furanose | + | Celibiose | – | D-Psicose | – |
| Salicin | + | Maltose | – | L-Sorbose | – |
| Acetic acid | – | Maltotriose | – | D-Manitol | – |
| Fumaric acid | – | Melezitose | – | D-Sorbitol | – |
| Propionic acid | – | Palatinose | – | D-Arabitol | – |
| Succinic acid | – | D-Rafinose | – | Xylitol | – |
| Methyl succinate | – | Stachyose | – | Glycerol | – |
| L-Aspartic acid | – | Sucrose | – | | |
| L-Glutamic acid | – | Trehalose | – | | |

+(F): intense coloration
+: coloration
–: absence of coloration

TABLE II

Assimilation tests

| | | | | | |
|---|---|---|---|---|---|
| Maltotriose | + | Inulin | – | Salicin | – |
| Sucrose | + | Cellobiose | – | Maltitol | – |
| Trehalose | + | Gentibiose | – | D-Sorbitol | – |
| Furanose | + | Melezitose | – | i-Erythritol | – |
| Manitol | + | Melibrose | – | Glycerol | – |
| D-Arabitol | + | Palatinose | – | L-Arabinose | – |
| Methyl succinate | + | Rafinose | – | D-Arabinose | – |
| Malic acid | + | Stachyose | – | D-Ribose | – |
| Maltose | + | Turanose | – | Methyl succinate + D-Xylose | – |
| Adonitol | + | N-acetyl-D-Glucosamine | – | Quinic acid + D-Xylose | – |
| Xylitol | + | D-Glucosamine | – | D-Glucoronic acid + D-Xylose | – |
| Xylose | + | Alpha-D-Glucose | – | Dextrin + D-Xylose | – |
| Fumaric acid | – | D-Galactose | – | Alpha-D-Lactose + D-Xylose | – |
| Bromosuccinic acid | – | D-Psicose | – | Alpha-D-Melibiose + D-Xylose | – |
| L-Glutamic acid | – | L-Manose | – | D-Galactose + D-Xylose | – |
| Alpha-aminobutyric acid | – | L-Sorbose | – | m-Inositol + D-Xylose | – |
| Alpha-Ketoglutaric acid | – | Alpha-methyl-D-Glucoside | – | 1,2-propanodiol + D-Xylose | – |
| 2-Keto-D-gluconic acid | – | Beta-methyl-D-Glucoside | – | Acetoin + D-Xylose | – |
| D-Gluconic acid | – | Amygdaline | – | | |
| Dextrin | – | Arbutine | – | | |

+: coloration
–: absence of coloration

Moreover, the CECT-10817 strain is resistant to the antibiotic streptomycin sulphate, at a concentration of 0.5 g/ml.

Figure 2:
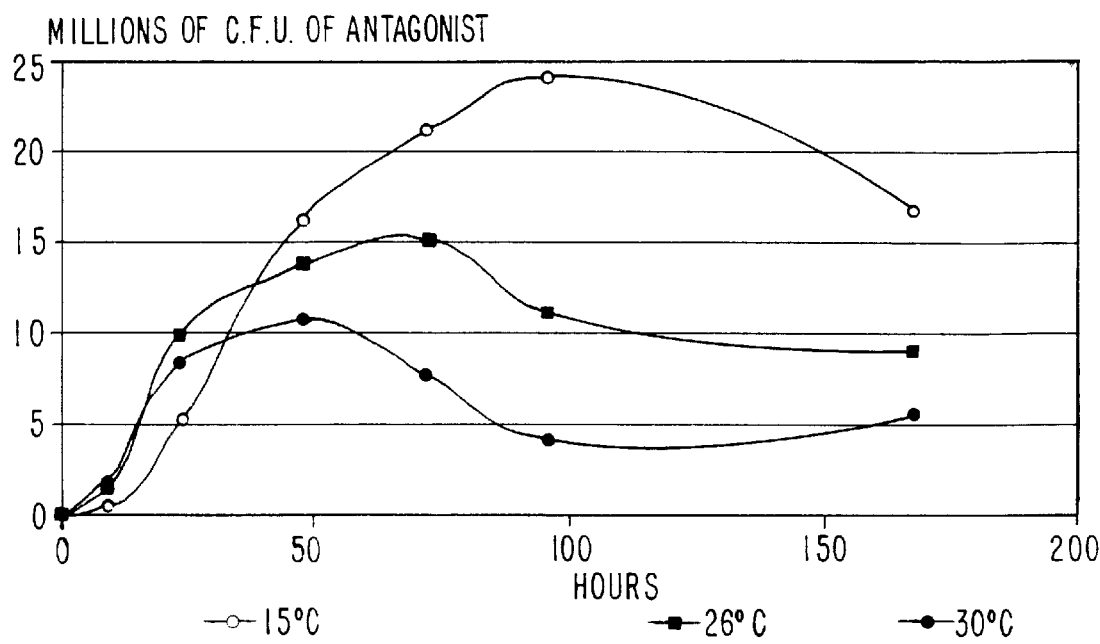
FIG. 2 is a graphic representation of the CECT-10817 strain, in NYDB medium, at temperatures of 15° C., 26° C. and 30° C.
Figure 3:
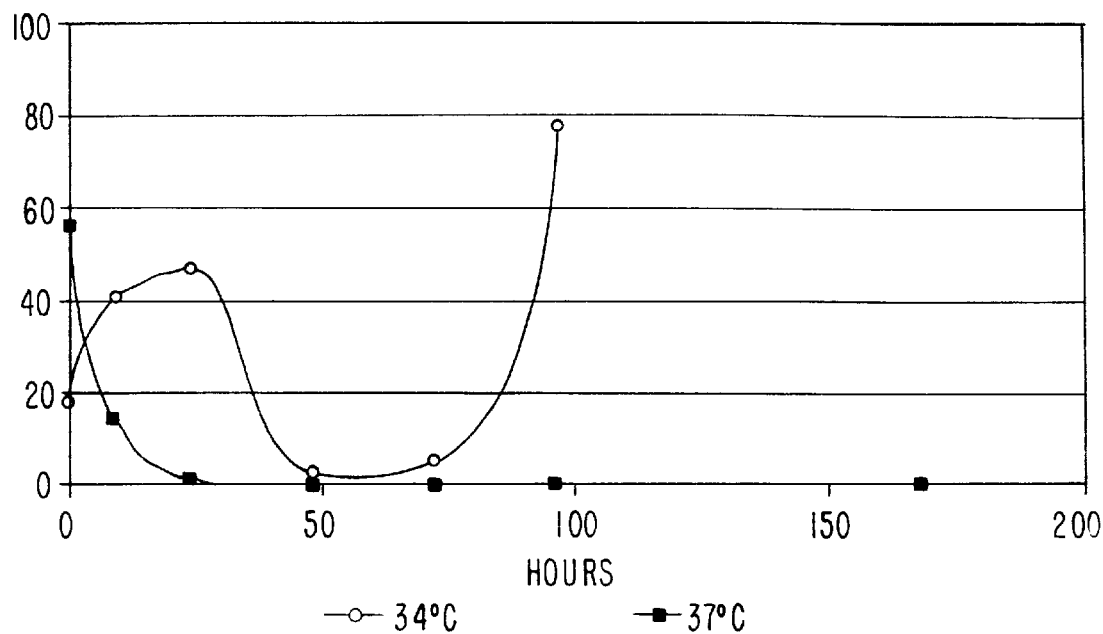
FIG. 3 is a graphic representation of the CECT-10817 strain, in NYDB medium, at temperatures of 34° C. and 37° C.

"In vitro" growth of the microorganism of the CECT-10817 strain, in NYDB medium, at pH 7, takes place under aerobic conditions over a broad range of incubation temperatures, showing satisfactory growth at temperatures between 1° C. and 34° C. As can be observed in FIGS. 1, 2 and 3, the population maximum is achieved at 1° C., this being very much higher than that which takes place at any of the other temperatures studied.

Figure 4:
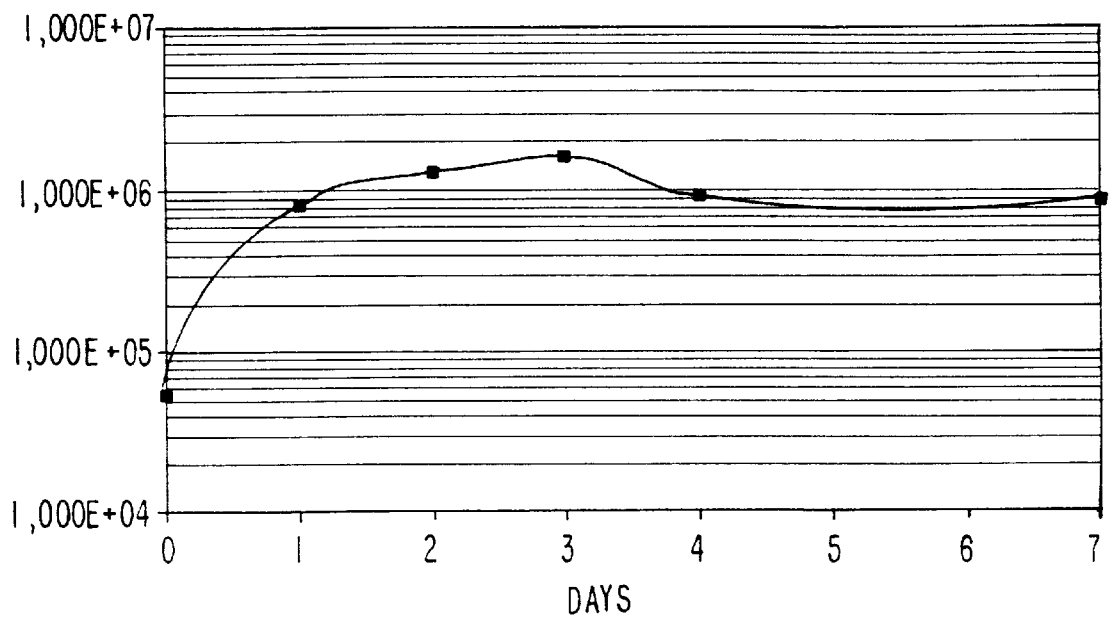
FIG. 4 is a graphic representation of the population development of the CECT-10817 strain on "Golden Delicious" apple at a temperature of 25° C.
Figure 5:
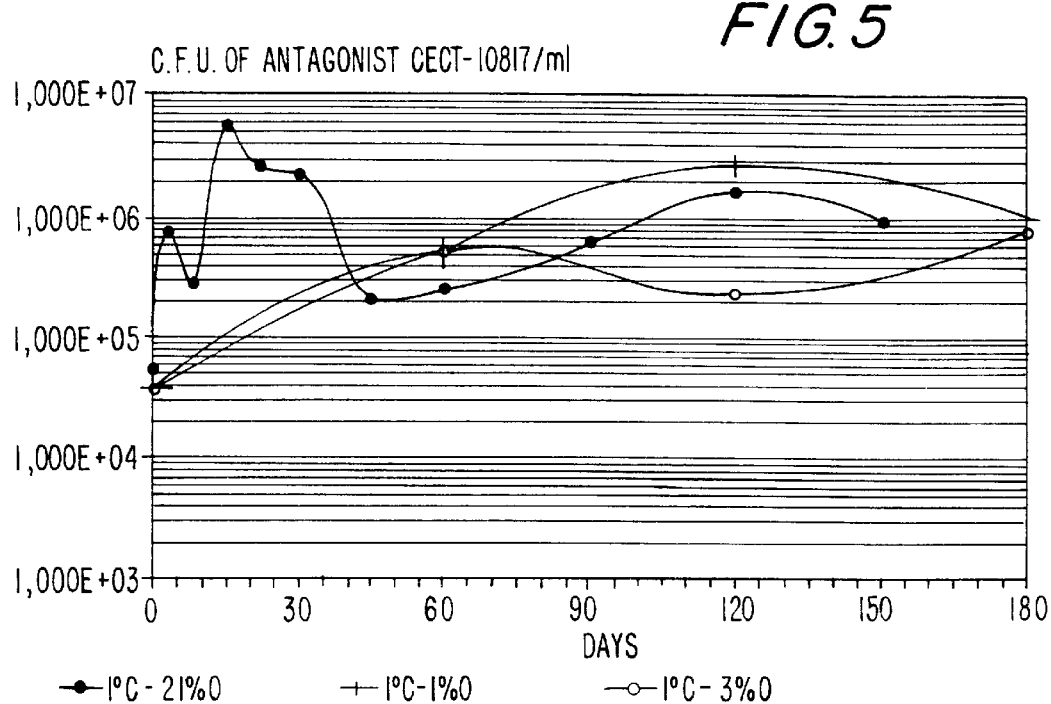
FIG. 5 is a graphic representation of the population development of the CECT-10817 strain on "Golden Delicious" apple under cold-storage conditions: in conventional cold (at temperature of 1° C., and in an atmosphere with oxygen content of 21%); in controlled atmosphere (at a temperature of 1° C. and in an atmosphere with oxygen content of 3%); and in a controlled ultra-low oxygen atmosphere (at temperature of 1° C. and in an atmosphere with oxygen content of 1%).

As shown by the graphics of FIGS. 4 and 5, the inoculation of the microorganism in fruit shows great growth in aerobic conditions, at both ambient temperature (25° C.) and at a temperature of 1° C., whether in ambient atmosphere (21% oxygen) or in controlled atmospheres with 3% oxygen and 1% oxygen (ultra-low oxygen), which are inherent to the storage conditions in fruit-horticultural centers.

The isolate of CECT-10817 strain can be obtained, in laboratories and for industrial use, by cultivation thereof in a suitable medium, by means of conventional techniques sufficiently known by experts. It can be obtained, for example, by cultivation of the original strain in NYDB medium at pH 7, in a receptacle which can be shaken and aerated, at temperatures between 1° C. and 34° C., for periods of time of the order of 20 to 50 hours. The population maximum for the NYDB medium is achieved at 37 hours at 25° C. Once the incubation period has finished the microorganisms are separated from the cultivation medium by conventional techniques of sedimentation, centrifuging or filtering, and the culture can be preserved by, for example, freezing with silica gel.

The antagonist CECT-10817 can be applied to the surface of the fruits by any conventional technique. For example, a dispersion of the culture in water can be prepared and the fruit sprayed or sprinkled in the field before harvesting, or the treatment can be applied during the handling process of the harvested fruit, before storage of same, in which case the treatment can also be implemented by immersion.

Figure 13:
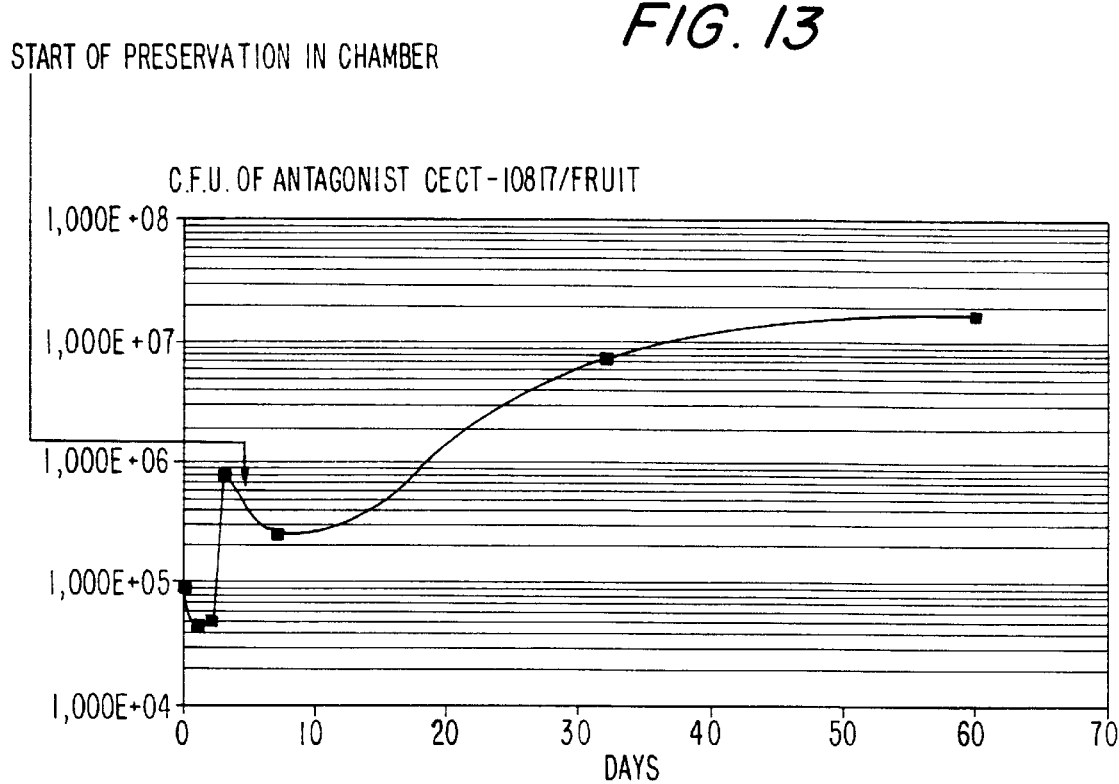
FIG. 13 is a graphic view of the population evolution of the antagonist CECT-10817 on "Golden Delicious" apples, applied in the field by spraying, throughout the process of harvesting, handling and preservation under conventional cold conditions (at temperature of 1° C., and in an atmosphere with oxygen content of 21%).

As can be seen in FIG. 13, when the fruits are treated by spraying of same while on the tree, the isolate of CECT-10817 strain maintains its viability or even increases its population on the surface of the fruit throughout the harvesting and storage process.

The effective concentrations of the antagonist CECT-10817 in the dispersion of application for the treatment of fruits can vary as a function of factors such as the type of fruit, its maturity, the concentration of pathogenic fungus on the fruit, the type of wound or injury affecting the fruit, the storage temperature and humidity, etc. The range of effective concentrations is usually between $10^5$ and $10^7$ c.f.u./ml (colony-forming units per milliliter), though this range should not be taken to restrict the scope of the present invention.

The isolate of CECT-10817 strain is very effective in the biological control of a large number of species of pathogenic fungi of fruits, including, through not restricted to, *Botrytis cinerea, Penicillium expansum* and *Rhizopus nigricans*. Its effectiveness in the prevention of rotting of fruit is not limited to storage of same under ambient conditions of temperature and oxygen concentration, but, owing to the above-mentioned characteristics of the microorganism, its use also provides excellent results under the cold-storage and controlled atmosphere conditions habitually used by industrial fruit-horticulture centers.

The effectiveness of the isolate of CECT-10817 strain in the control of pathogenic fungi is comparable to that of the fungicide Imazalil, a chemical product derived from imidazol (1-[2-(2,4-dichlorophenyl)-2-(2-propenyloxi)ethyl]-1H-imidazol), one of the fungicides most widely used worldwide in the post-harvesting of fruits, which means that the isolate of CECT-10817 strain constitutes an effective alternative for the chemical product, with the advantage that it lacks the toxicity characteristics of Imazalil.

The isolate of CECT-10817 strain can be employed effectively to combat rotting of all types of fruits in any of their varieties, especially pip fruits such as apples, pears and quinces; citrus fruits such as oranges, lemons and mandarins; stone fruits such as peaches, apricots and plums; and other fruits, such as strawberries.

The authors of the present invention are not aware, up to the present invention, of any report on any specific antagonist biological control agent against pathogenic fungi of the species *Rhizopus nigricans*. The species is very aggressive in pathological terms, for it possesses pectinolytic enzymes which permit it to break down the tissue of the fruit without the infection requiring wounds or injuries for its onset. It can for this reason cause rotting in healthy fruits in the event of contact of same with affected fruits (nest effect). Furthermore, the rotting which this species causes develops very rapidly and is characterized in that the tissues of the fruit become very watery and soft so that, due to the giving off of a large volume of contaminated liquid, the infection spreads easily to the other stored crates. For these reasons, the presence of *Rhizopus nigricans* in an industrial cold-storage chamber produces very high percentages of rotting. Moreover, to the knowledge of the authors of the present invention, there exists no specific chemical fungicide against *Rhizopus nigricans*.

This situation means that, in Spain for example, a country with high fruit-horticulture production, the fungi of the species *Rhizopus nigricans* are becoming one of the most dangerous pathogens, causing serious losses in the post-harvesting of pip fruits.

It should therefore be stressed that the antagonist CECT-10817, object of the present invention, constitutes the first effective treatment reported for combatting the pernicious effects produced by fungi of the aforesaid species *Rhizopus nigricans*.

EXAMPLES

The examples outlined below should be interpreted as an aid to better understanding of the invention, and not as limitations to the scope of same.

Example 1

Making an Aqueous Dispersion of CECT-10817

The antagonist CECT-10817 was implanted in a test tube with NYDA medium and incubated at 25° C. for 24–48 hours. Then, using the contents of the test tube, it was implanted in an Erlenmeyer flask with 50 ml of NYDB medium which was incubated in an orbital agitator at 150 rpm and 25° C. for 24 hours. The contents of the flask were then centrifuged at 6,000 rpm for 10 minutes and the floating part removed. The sediment was dispersed in 50 ml of sterile distilled water and that dispersion used to prepare the desired concentrations of the antagonist by calculating the transmittance of the microbial suspension in a spectrophotometer, as an indirect measurement of the concentration of the antagonist. The equivalence between the transmittance and the concentration of microorganisms was implemented using a Thoma microorganism-count chamber. The concentrations are expressed in c.f.u./ml (colony-forming units per milliliter).

Example 2

Effectiveness of CECT-10817 on Fruits stored at ambient temperature

The test was carried out on healthy "Golden Delicious" apples which were cleaned with water and left to dry, following which two perforations per apple were made, of dimensions of approximately 3×3×3 mm. The two incisions were situated on the same side of the apple, one on the top part and one on the bottom. The sample unit was made up of three apples, and three repetitions were made for each treatment.

The three fungic species tested were *Botrytis cinerea, Penicillium expansum* and *Rhizopus nigricans*, and titration of the suspensions of spores of same was carried out using young 5–7 day cultures implanted in PDA medium (potato, dextrose and agar) and incubated at temperature of 28° C., by scraping of the colonies into sterile distilled water with Tween 80. A spore count was then carried out in a Thoma chamber, setting the desired concentration, expressed in c.f.u./ml.

Batches of three apples prepared as explained above were inoculated with 25 $\mu$l of the suspension of CECT-10817 antagonist, at concentrations of $2.62 \times 10^6$ c.f.u./ml, $7.0 \times 10^6$ c.f.u./ml and $1.15 \times 10^7$ C.f.u./ml. Once the fruits were dry, they were inoculated with 20 $\mu$l of the titrated suspensions of pathogens of the three species selected, at concentrations of $10^3$ c.f.u./ml, $10^4$ c.f.u./ml and $10^5$ c.f.u./ml. In parallel to this the control test was set up, in which apples were inoculated only with the titrated suspension of the pathogen and sterile distilled water.

All the treated fruits were placed in alveoli, left to dry and then placed in boxes for incubation at 20° C. in ambient atmosphere. For the fruits inoculated with *Penicillium expansum* the incubation time was seven days, while for *Botrytis cinerea* it was six days and for *Rhizopus nigricans* it was five days. The incubation period was set on the basis of the time needed for the control apples to present large rotting diameters. Following said incubation period the results were read, by measuring the diameters of rot of all the perforations made.

The rot diameter readings of the various repetitions were subjected to a statistical analysis consisting in analysis of the variance and, once it was found that the variance analysis was significant ($\alpha<0.01$ to $\alpha<0.05$), a separation of averages was carried out using the Duncan Multiple Range Test, the results of which are expressed with the lower-case letters of the alphabet (a, b, c, d, etc.), in such a way that treatments with the same letter are statistically equal and treatments with different letters are statistically different.

Table III shows the results obtained in the case of biological control of *Botrytis cinerea*, Table IV the results with *Pencillium expansum* and Table V the results with *Rhizopus nigricans*.

Figure 6:
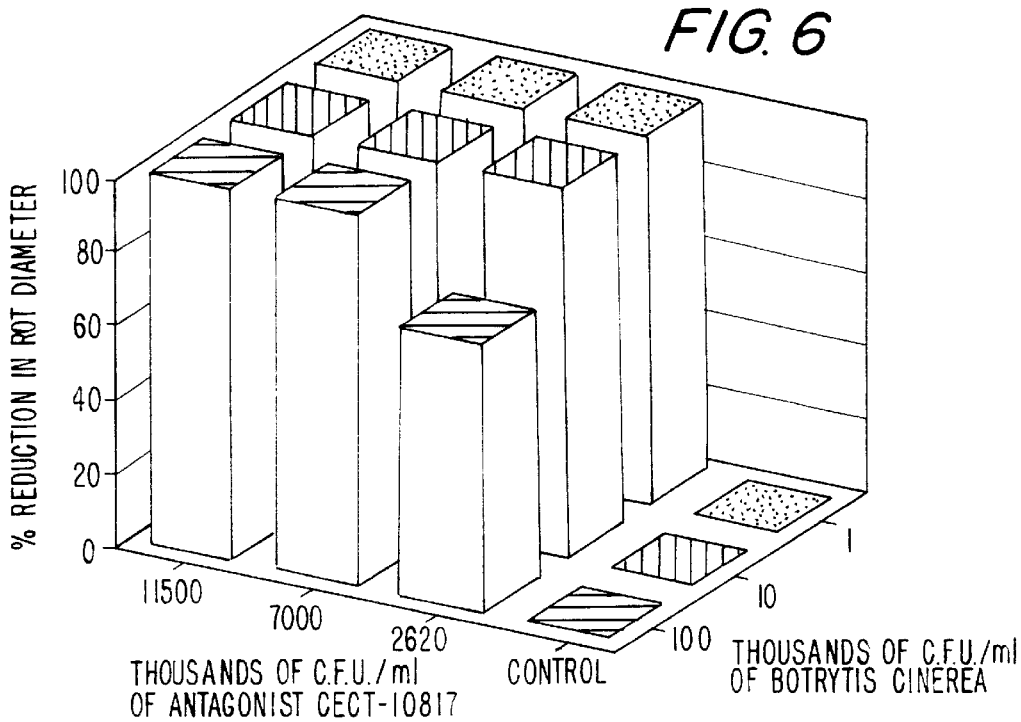
FIG. 6 is a three-dimensional bar-diagram view of the percentages of reduction of rotting, in "Golden Delicious" apples inoculated with *Botrytis cinerea*, caused by inoculation of the antagonist CECT-10817. Data obtained following six days of incubation at 20° C.

The graphical illustrations of the results in these Tables are to be found in FIGS. 6, 7 and 8, respectively.

TABLE III

Control of CECT-10817 on *B. cinerea*

| CONCENTRAT. c.f.u./ml *Botrytis cinerea* | MEASUREMENT | CONTROL 0 | CECT-10817 DOSE c.f.u./ml | | |
|---|---|---|---|---|---|
| | | | $2.62 \cdot 10^6$ | $7.0 \cdot 10^6$ | $1.15 \cdot 10^7$ |
| $10^3$ | AVERAGE ROT DIAM. (cm) | 0.14 a | 0.00 b | 0.00 b | 0.00 b |
| | % REDUCTION IN ROT DIAMETER | — | 100% | 100% | 100% |
| $10^4$ | AVERAGE ROT DIAM. (cm) | 1.29 a | 0.00 b | 0.00 b | 0.00 b |
| | % REDUCTION IN ROT DIAMETER | — | 100% | 100% | 100% |
| $10^5$ | % AVERAGE ROT DIAM. (cm) | 2.08 a | 0.58 b | 0.00 c | 0.00 c |
| | % REDUCTION IN ROT DIAMETER | — | 72.18% | 100% | 100% |

TABLE IV

Control of CECT-10817 on *P. expansum*

| CONCENTRAT. c.f.u./ml *Penicillium expansum* | MEASUREMENT | CONTROL 0 | CECT.10817 DOSE c.f.u./ml | | |
|---|---|---|---|---|---|
| | | | $2.62 \cdot 10^6$ | $7.0 \cdot 10^8$ | $1.15 \cdot 10^7$ |
| $10^3$ | AVERAGE ROT DIAM. (cm) | 1.64 a | 0.11 b | 0.00 b | 0.00 b |
| | % REDUCTION IN ROT DIAMETER | — | 92,25% | 100% | 100% |
| $10^4$ | AVERAGE ROT DIAM. (cm) | 2.34 a | 1.08 b | 0.45 c | 0.64 c |
| | % REDUCTION IN ROT DIAMETER | — | 53.70% | 80.76% | 72.68% |
| $10^5$ | AVERAGE ROT DIAM. (cm) | 2.65 a | 1.74 b | 0,73 c | 0.76 c |
| | % REDUCTION IN ROT DIAMETER | — | 34.38% | 72.53% | 71.28% |

TABLE V

Control of CECT-10817 on R. nigricans

| Rhizopus nigricans CONCENTRAT. c.f.u./ml | MEASUREMENT | CONTROL 0 | CECT-10817 DOSE c.f.u./ml | | |
|---|---|---|---|---|---|
| | | | $2.62 \cdot 10^6$ | $7.0 \cdot 10^6$ | $1.15 \cdot 10^7$ |
| $10^3$ | AVERAGE ROT DIAM. (cm) | 5.05 a | 0.22 b | 0.00 b | 0.00 b |
| | % REDUCTION IN ROT DIAMETER | — | 96.41% | 100% | 100% |
| $10^4$ | AVERAGE ROT DIAM. (cm) | 7.38 a | 1.58 b | 0.20 c | 0.00 c |
| | % REDUCTION IN ROT DIAMETER | — | 78.63% | 97.29% | 100% |
| $10^5$ | AVERAGE ROT DIAM. (cm) | 8.07 a | 2.01 b | 0.10 c | 0.22 c |
| | % REDUCTION IN ROT DIAMETER | — | 75.09% | 98.76% | 97.31% |

The data shown in the above-mentioned Tables III, IV and V, together with their graphic representation in FIGS. 6, 7 and 8, show the high effectiveness of the antagonist CECT-10817 in control of the three species of pathogenic fungi tested and, consequently, in control of rotting of the fruits.

If a comparison of the results obtained is made with the description of North American patent application U.S. Pat. No. 7,745,796 (Wilson), mentioned above, of special significance is that fact that the efficacy of the *Candida sake* CECT-10817 strain is clearly greater, in the case of control of the species *Botrytis cinerea* and *Penicillium expansum*, than that shown by the *Candida sake* NRRL Y-18844, NRRL Y-18845 and NRRL Y18846 strains described in said patent application.

Example 3

Effectiveness of CECT-10817 on Fruits stored at low temperatures and different oxygen atmospheres Following the working method explained in example 2, tests were carried out with twenty "Golden Delicious" apples per repetition and three repetitions per treatment.

25 μl of aqueous dispersion of the antagonist CECT-10817 were inoculated, at the three concentrations used in example 2, and 20 μl of *Penicillium expansum* inoculant, at a concentration of $10^4$ c.f.u./ml. Three batches of inoculated apples were then separated and stored for sixty days: one batch under conventional cold-storage conditions (1° C. and ambient oxygen), another batch under controlled atmosphere conditions (1° C. and 3% oxygen) and the last batch under ultra-low oxygen conditions (1° C. and 1% oxygen).

The results were read, processed statistically in the same way as for example 2 and set out in Tables VI, VII and VIII. Their joint graphic representation is set out in FIG. 9.

TABLE VI

Storage at 1° C. and 21% $O_2$

| MEASUREMENT | CONTROL 0 | CECT-10817 DOSE c.f.u./ml | | |
|---|---|---|---|---|
| | | $2.62 \cdot 10^6$ | $7.0 \cdot 10^6$ | $1.15 \cdot 10^7$ |
| AVERAGE ROT DIAM. (cm) | 3.92 a | 2.01 b | 1.45 bc | 1.11 c |
| % REDUCTION IN ROT DIAMETER | — | 48.59% | 62.96% | 71.74% |

TABLE VII

Storage at 1° C. and 3% $O_2$

| MEASUREMENT | CONTROL 0 | CECT-10817 DOSE c.f.u./ml | | |
|---|---|---|---|---|
| | | $2.62 \cdot 10^6$ | $7.0 \cdot 10^6$ | $1.15 \cdot 10^7$ |
| AVERAGE ROT DIAM. (cm) | 4.13 a | 0.89 b | 0.42 bc | 0.10 d |
| % REDUCTION IN ROT DIAMETER | — | 78.30% | 89.79% | 94.45% |

TABLE VIII

Storage at 1° C. and 1% $O_2$

| MEASUREMENT | CONTROL 0 | CECT-10817 DOSE c.f.u./ml | | |
|---|---|---|---|---|
| | | $2.62 \cdot 10^6$ | $7.0 \cdot 10^6$ | $1.15 \cdot 10^7$ |
| AVERAGE ROT DIAM. (cm) | 2.87 a | 1.30 b | 0.84 bc | 0.62 c |

TABLE VIII-continued

Storage at 1° C. and 1% $O_2$

| MEASUREMENT | CONTROL 0 | CECT-10817 DOSE c.f.u./ml | | |
|---|---|---|---|---|
| | | $2.62 \cdot 10^6$ | $7.0 \cdot 10^6$ | $1.15 \cdot 10^7$ |
| % REDUCTION IN ROT DIAMETER | — | 64.05% | 70.05% | 78.43 |

Figure 9:
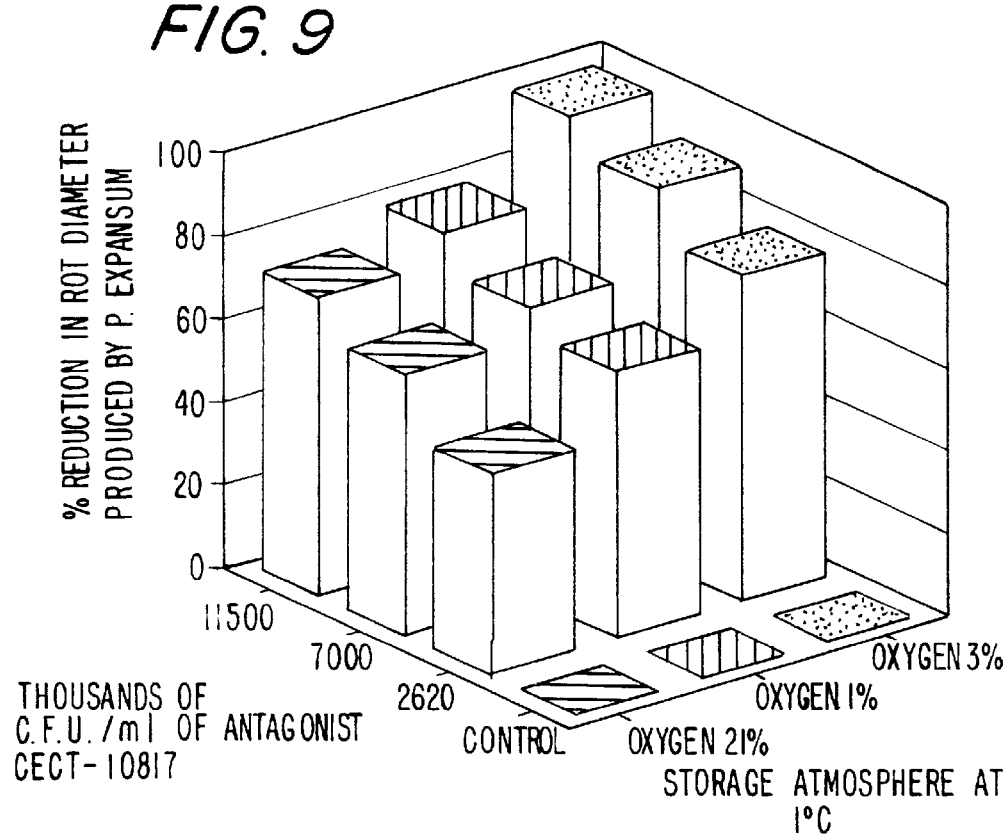
FIG. 9 is a three-dimensional bar-diagram view of the percentages of reduction of rotting, in "Golden Delicious" apples inoculated with *Penicillium expansum*, caused by inoculation of the antagonist CECT-10817. Data obtained following sixty days of incubation under cold-storage conditions: in conventional cold (at temperature of 1° C., and in an atmosphere with oxygen content of 21%); in controlled atmosphere (at a temperature of 1° C. and in an atmosphere with oxygen content of 3%); and in a controlled ultra-low oxygen atmosphere (at temperature of 1° C. and in an atmosphere with oxygen content of 1%).

As can be observed in the above tables and in FIG. 9, the results obtained show a high degree of efficacy in the control of *P. expansum* under conventional cold-storage conditions, while the efficacy is notably increased when the tests are carried out under low-temperature storage and low-oxygen environment conditions.

Example 4

Control of B. cinerea under conventional cold-storage conditions

A test was carried out, under the same conditions as example 3, using as pathogenic fungus 20 μl of *Botrytis cinerea* inoculant, at a concentration of $10^4$ c.f.u./ml. The test was carried out under conventional cold-storage conditions (1° C. and ambient oxygen).

Figure 10:
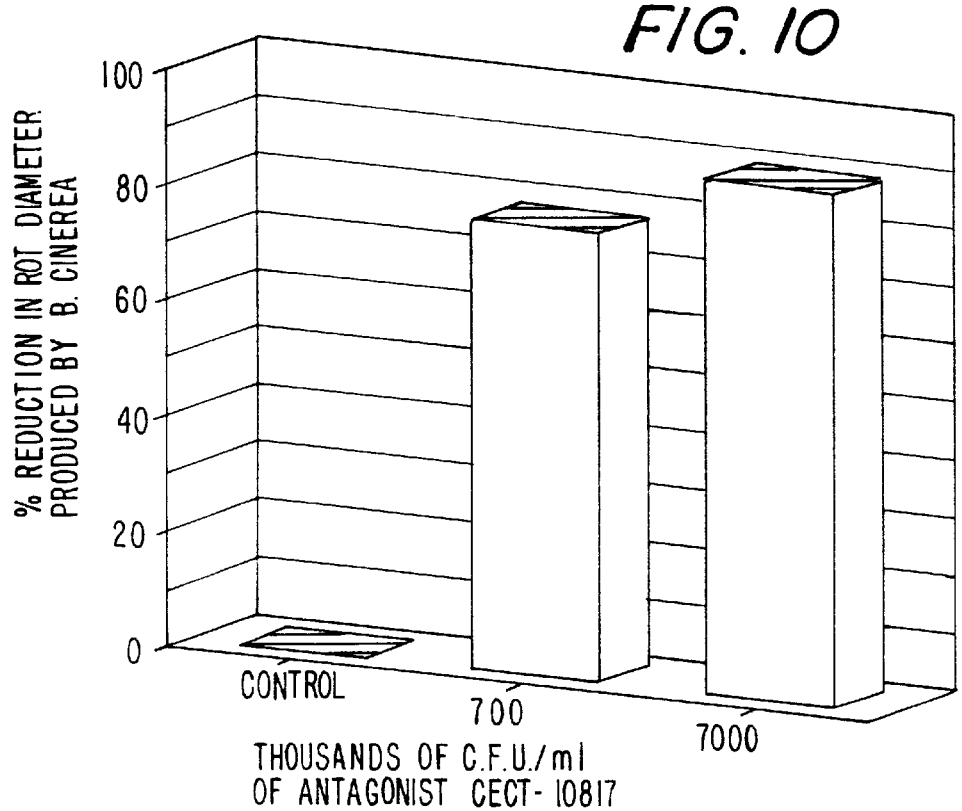
FIG. 10 is a three-dimensional bar-diagram view of the percentages of reduction of rotting, in "Golden Delicious" apples inoculated with *Botrytis cinerea*, caused by inoculation of the antagonist CECT-10817. Data obtained following sixty days of incubation under conventional cold conditions (at temperature of 1° C., and in an atmosphere with oxygen content of 21%).

The results obtained, following the above-mentioned statistical processing, are set out in Table IX, with graphic representation thereof in FIG. 10.

TABLE IX

Control of *Botrytis cinerea* at 1° C. and 21% $O_2$

| MEASUREMENT | CONTROL 0 | CECT-10817 DOSE c.f.u./ml | |
|---|---|---|---|
| | | $7.0 \cdot 10^5$ | $7.0 \cdot 10^6$ |
| AVERAGE ROT DIAM. (cm) | 1.30 a | 0.39 b | 0.14 b |
| % REDUCTION IN ROT DIAMETER | – | 77.7% | 89.2% |

The rot diameter reduction results were excellent, especially at a concentration of CECT-10817 inhibitor of $7 \times 10^6$ c.f.u./ml.

Example 5

Control of *Penicillium expansum* in large-scale test

For this test the dispersion of antagonist was prepared on a larger scale, in the following manner:

The antagonist CECT-10817 was implanted in a test tube with NYDA medium and was incubated at 25° C. for 24–48 hours. The contents of this test tube were then implanted in a fermenter fitted with an agitator and an aeration system, with 2,000 ml of NYDB medium and incubated at 25° C. for 37 hours. The contents of the fermenter were then centrifuged at 6,000 rpm for 10 minutes and the floating matter removed. The sediment was dispersed in sterile distilled water and that dispersion used to prepare the desired concentrations of the antagonist in the same way as for example 1.

One box of "Golden Delicious" apples (70 fruits) was used per repetition and four repetitions per treatment. The apples collected in the field were perforated in their equatorial zone (4 incisions per apple) with a scalpel and were treated with the CECT-10817 antagonist, by lowering the boxes with the fruit into baths containing dispersions of antagonist at concentrations of $7 \times 10^5$ and $7 \times 10^6$ c.f.u./ml. An untreated control batch was also used. Then, once the apples were dry, the boxes were lowered into a batch with a titrated dispersion of spores of *Penicillium expansum* at a concentration of $10^4$ c.f.u./ml.

The boxes of apples were stored for sixty days under cold-storage conditions (1° C. and ambient oxygen), at the end of which the results were read under the same conditions and with the same statistical processing as in the previous examples.

Figure 11:
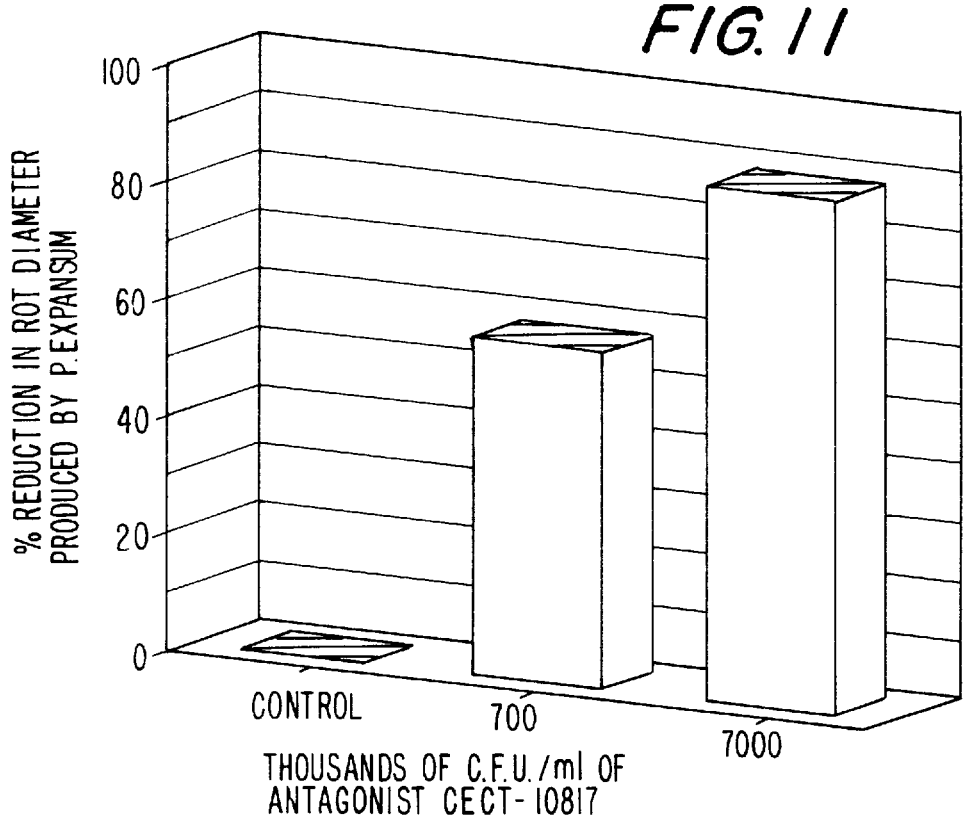
FIG. 11 is a three-dimensional bar-diagram view of the percentages of reduction of rotting, in "Golden Delicious" apples inoculated with *Penicillium expansum*, caused by bathing the fruits with the antagonist CECT-10817. Data obtained following sixty days of large-scale testing under conventional cold conditions (at temperature of 1° C., and in an atmosphere with oxygen content of 21%).

The results are set out in Table X, with graphic representation thereof in FIG. 11.

TABLE X

Control of *P. expansum* on a large scale

| MEASUREMENT | CONTROL 0 | CECT-10817 DOSE c.f.u./ml | |
|---|---|---|---|
| | | $7.0 \cdot 10^5$ | $7.0 \cdot 10^6$ |
| AVERAGE ROT DIAM. (cm) | 1.20 a | 0.51 b | 0.14 c |
| % REDUCTION IN ROT DIAMETER | — | 57.5% | 88.0% |

As the aforesaid table and figure show, the large-scale test confirmed the excellent results in control of *P. expansum* obtained in the previous tests. It is noteworthy that the reduction of rot diameter is practically 90% when a CECT-10817 antagonist concentration of $7 \times 10^6$ c.f.u./ml is used.

Example 6

Comparison with the Fungicide Imazalil

The test was carried out with twenty "Golden Delicious" apples per repetition and three repetitions per treatment, with five perforations being made in each fruit.

Both CECT-10817 antagonist and Imazalil fungicide were applied by bathing the fruits in solutions or dispersions of same. The antagonist was applied at a concentration of $7 \times 10^6$ c.f.u./ml and the Imazalil at a concentration of 7.5% by weight.

The apples were then inoculated with the pathogen of the species *Penicillium expansum* at a concentration of $10^4$ c.f.u./ml. In one batch of the apples treated with the antagonist, inoculation of the pathogen was carried out 24 hours after the treatment.

The fruits were incubated at 20° C. for eight days, at the end of which the results were read and processed statistically.

Figure 12:
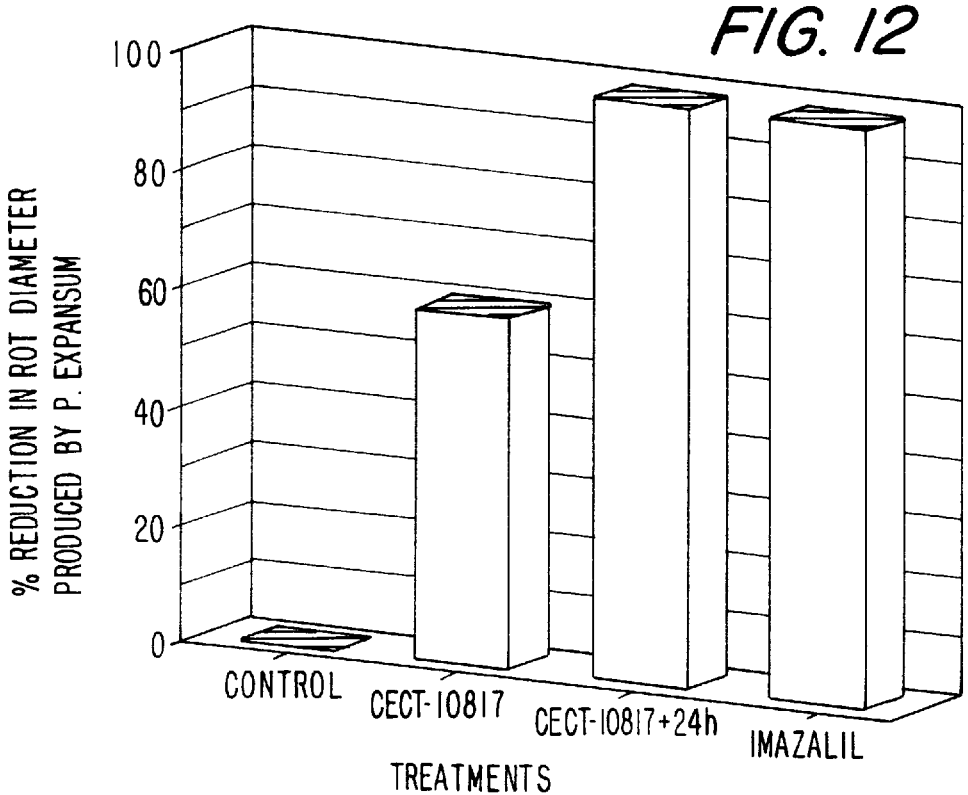
FIG. 12 is a three-dimensional bar-diagram view of the percentages of reduction of rotting, in "Golden Delicious" apples inoculated with *Penicillium expansum*, caused by spraying with $7 \times 10^6$ c.f.u./ml of the antagonist CECT-10817 and by application of the chemical fungicide Imazalil at a concentration of 7.5%. Comparative data obtained following eight days of incubation at temperature of 20° C.

The results obtained are shown in Table XI, with graphic representation thereof in FIG. 12.

TABLE XI

Control of *P. expansum*, comparison with Imazalil

| MEASUREMENT | CONTROL | IMAZALIL (Dose 7.5%) | CECT-10817 ($7.0 \cdot 10^6$ c.f.u./ml) | CECT-10817 + 24 hours ($7.0 \cdot 10^6$ c.f.u./ml) |
|---|---|---|---|---|
| AVERAGE ROT DIAM. (cm) | 2.489 a | 0.046 c | 1.046 b | 0.041 c |
| % REDUCTION IN ROT DIAMETER | — | 98.15% | 59.42% | 98.30% |

It can be observed that when inoculation of the antagonist takes place 24 hours after the treatment, the effectiveness of the CECT-10817 antagonist and the Imazalil is practically the same.

Information on Depositing of the CECT-10817 Strain

The microorganism was deposited in accordance with the provisions of the Treaty of Budapest on recognition of the depositing of microorganisms for the purpose of patent procedure, at the international depositing authority Colecci ón Española de Cultivos Tipo (CECT), situated at the Department of Microbiology, Faculty of Biological Sciences, University of Valencia, 46100 Burjasot (Valencia) . The deposit was made on 6 Jul. 1994 and the CECT assigned it deposit number CECT-10817.

The deposit is at the disposal of the public, under the conditions provided for in the aforesaid Treaty of Budapest, although this availability cannot be interpreted as a licence to put into practice the object of the present invention, infringing the rights of the applicant for the present patent.

We claim:

1. A substantially pure biological culture of *Candida sake*, CECT-10817.

2. A method for preventing rotting of fruits, comprising treating the fruits, before or after harvesting, with an effective amount of the culture of claim 1.

3. The method, as defined in claim 2, wherein the treatment is carried out by means of spraying, wetting, or immersion of the fruits in or with an aqueous dispersion of the culture.

4. The method, as defined in claim 2, wherein the concentration of the *Candida sake* CECT-10817 in the aqueous dispersion ranges between $10^5$ and $10^7$ cfu/ml.

5. The method as defined in claim 2, further comprising, after said treating, storing said fruits at ambient conditions of temperature and oxygen.

6. The (A) method, as defined in claim 2, further comprising, after said treating, storing said fruits at a temperature lower than 5° C. and in an atmosphere with an oxygen content lower than 5%.

7. A method of preventing rotting of fruit caused by at least one pathogenic fungus, after or before harvesting the fruit, said method comprising the steps of:

a) making an aqueous dispersion containing *Candida sake* CECT-10817; and b) treating the fruit to be protected against rotting with an effective amount of said aqueous dispersion.

8. The method as defined in claim 7, wherein said treating is performed by means of spraying the fruit with the aqueous dispersion, wetting the fruit with the aqueous dispersion, immersing the fruit in the aqueous dispersion and/or inoculating the fruit with the aqueous dispersion.

9. The method as defined in claim 7, wherein said at least one pathogenic fungus is a member selected from the group consisting of *Botrytis cinera, Penicillium expansum* and *Rhizopus nigricans*.

10. The method, as defined in claim 7, wherein said at least one pathogenic fungus is *Rhizopus nigricans*.

11. The method as defined in claim 7, wherein said aqueous dispersion is made from a culture prepared by cultivation of said strain at pH 7 in NYDB culture medium at temperatures between 1° C. and 34° C. for 20 to 50 hours and said aqueous dispersion contains between $10^5$ and $10^7$ c.f.u./ml of said strain.

12. The method as defined in claim 7, further comprising, after said treating, storing said fruit at ambient conditions of temperature and oxygen.

13. The method as defined in claim 7, further comprising, after said treating, storing said fruit at a temperature less than 5° C.

14. The method as defined in claim 13, further comprising, after said treating, storing said fruit in an atmosphere with an oxygen content of less than 5%.

15. The method as defined in claim 7, wherein said fruit is strawberries, a pip fruit, a citrus fruit or a stone fruit.

16. The method as defined in claim 15, wherein said pip fruit is apples, pears or quinces.

17. The method as defined in claim 15, wherein said citrus fruit is oranges, lemons or mandarins.

18. The method as defined in claim 15, wherein said stone fruit is peaches, apricots or plums.

19. A method of preventing rotting of fruit caused by *Rhizopus nigricans* after or before harvesting the fruit, said method comprising the steps of:

a) making an aqueous dispersion containing from about $10^5$ to $10^7$ cfu/ml of *Candida sake* CECT- 10817; and b) treating the fruit to be protected against rotting with an effective amount of said aqueous dispersion.

20. The method as defined in claim 19, further comprising storing said fruit at a temperature less than 5° C. after said treating.

21. The method as defined in claim 19, wherein said fruit is pip fruit.

\* \* \* \* \*